(12) United States Patent
Hsiao

(10) Patent No.: US 8,147,097 B1
(45) Date of Patent: Apr. 3, 2012

(54) ANGLE-ADJUSTABLE AROMA-DIFFUSING NIGHT LAMP SYSTEM

(76) Inventor: Ming Jen Hsiao, Toufen (TW)

(*) Notice: Subject to any disclaimer, the term of this patent is extended or adjusted under 35 U.S.C. 154(b) by 0 days.

(21) Appl. No.: 12/981,920

(22) Filed: Dec. 30, 2010

(51) Int. Cl.
*H01R 33/00* (2006.01)
*H01R 39/00* (2006.01)

(52) U.S. Cl. ........ 362/288; 362/640; 362/641; 362/436; 439/11

(58) Field of Classification Search .......... 362/640–641, 362/43, 285, 287, 288; 439/11, 13
See application file for complete search history.

(56) References Cited

U.S. PATENT DOCUMENTS

| | | | | |
|---|---|---|---|---|
| 6,276,813 B1* | 8/2001 | Victor | ............................ | 362/641 |
| 7,303,327 B2* | 12/2007 | Copeland et al. | ............. | 362/640 |
| 8,066,420 B2* | 11/2011 | Hsiao | ............................ | 362/640 |
| 2005/0018426 A1* | 1/2005 | Dickie | ........................... | 362/287 |

* cited by examiner

*Primary Examiner* — Ali Alavi
(74) *Attorney, Agent, or Firm* — Chun-Ming Shih

(57) ABSTRACT

An angle-adjustable aroma-diffusing night lamp system includes an electrical plug unit, a lamp socket unit, a collar coupled to a front coupling neck of the housing of the electrical plug unit and affixed to the housing of the lamp socket unit for allowing rotation of the lamp socket unit relative to the electrical lug unit within a predetermined angle, a spring-supported latch installed in the housing of the electrical plug unit to lock the electrical plug unit to the collar in one of a series of angular position, and a lampshade coupled to the lamp socket unit around the lamp bulb in the lamp socket unit and holding a fluid aroma substance for heating by the radiation heat from the lamp bulb into vapor.

10 Claims, 11 Drawing Sheets

ANGLE-ADJUSTABLE AROMA-DIFFUSING NIGHT LAMP SYSTEM

BACKGROUND OF THE INVENTION

1. Field of the Invention

This invention relates aroma diffusing night lamp system and more particularly, to an angle-adjustable aroma diffusing night lamp system that allows easy adjustment of the electrical plug relative to the lamp socket to one of a series of angular positions within a predetermined range.

2. Description of the Related Art

Conventional night lamp does not allow adjustment of the angular position of the two parallel metal prongs of their electric plugs to fit different indoor installation requirements.

There are night lamps with an added aroma diffusing function. These night lamps combine an angle-adjustable night lamp unit and an aroma diffuser unit. When the night lamp unit of a night lamp is connected to a city power supply outlet, the radiating heat from the night lamp unit heats an aromatic substance, for example, essential oil in the aroma diffuser unit into vapor, providing a romantic atmosphere and enhancing the value of use of the night lamp.

Although conventional aroma diffusing night lamps allow adjustment of the installation angle of the night lamp unit, their angle-adjustable structure wears quickly with use or is difficult to be adjusted to the accurate angle. After installation, the applied essential oil may fall from the lampshade accidentally.

Further, regular aroma diffusing night lamps commonly use an incandescent lamp bulb to emit light and to heat the supplied aromatic substance. The heating efficiency of an incandescent lamp is low. Further, the aroma diffuser unit of a regular aroma diffusing night lamp is less stable. In consequence, a gap may be produced in the electric conducting structure, affecting the performance of electric conductivity. Further, regular aroma diffusing night lamps have no means to seal the electric conducting component parts. If the aromatic fluid leaks out, a short circuit accident may occur.

U.S. Ser. No. 12/698,610 discloses an adjustable night lamp system, issued to the present inventor, entitled "AROMA DIFFUSING NIGHT LAMP SYSTEM HAVING AN ANGLE-ADJUSTABLE ELECTRIC PLUG", which comprises an electrical plug unit, which includes housing having a stepped rear coupling portion and an electrically insulative locating block tightly fitted into a front opening of the electrically insulative plug housing to hold first and second metal conducting blades and a grounding prong, a lamp socket unit for holding a lamp bulb and transferring electric current from the electrical plug unit to the lamp bulb for causing the lamp bulb to emit light, and a collar configured subject to the configuration of the stepped rear coupling portion of the electrically insulative plug housing and coupled to the stepped rear coupling portion and affixed to the lamp socket unit to secure the lamp socket unit to the electrical plug unit and to allow adjustment of the angle of the lamp socket unit relative to the electrical plug unit.

U.S. Ser. No. 12/911,939 discloses an adjustable night lamp system, issued to the present inventor, entitled "ANGLE-ADJUSTABLE NIGHT LAMP ASSEMBLY FOR AROMA DIFFUSING NIGHT LAMP SYSTEM", which comprises a lamp socket, a light emitting device mounted in the top side of the lamp socket, an electric plug rotatably coupled to the lamp socket and a lampshade surrounding the light emitting device and having a top trough that holds an aromatic substance that gives off a pleasant smell when heated by heat energy from the light emitting device during its operation".

SUMMARY OF THE INVENTION

The present invention has been accomplished under the circumstances in view. It is therefore the main object of the present invention to provide an angle-adjustable aroma-diffusing night lamp system, which allows easy adjustment of the electrical plug relative to the lamp socket to one of a series of angular positions within a predetermined range. It is another object of the present invention to provide an angle-adjustable aroma-diffusing night lamp system, which is safe in use.

To achieve these and other objects of the present invention, an angle-adjustable aroma-diffusing night lamp system comprises an electrical plug unit, a lamp socket unit, a collar coupled to a front coupling neck of the housing of the electrical plug unit and affixed to the housing of the lamp socket unit for allowing rotation of the lamp socket unit relative to the electrical lug unit within a predetermined angle, a spring-supported latch installed in the housing of the electrical plug unit to lock the electrical plug unit to the collar in one of a series of angular position, and a lampshade coupled to the lamp socket unit around the lamp bulb in the lamp socket unit and holding a fluid aroma substance for heating by the radiation heat from the lamp bulb into vapor.

Further, the electrical plug unit comprises a grounding prong arranged in a parallel manner relative to the positive contact blade and the negative contact blade for grounding.

Further, the housing of the housing of the lamp socket unit consists of an upper socket housing cover shell and a lower socket housing cover shell that are fastened together with a self-tapping screw.

Further, the collar comprises a plurality of equiangularly spaced latch holes; the electrical plug unit further comprises a spring member mounted in the housing thereof, and a latch supported on the spring member and selectively engaged into one of the latch holes to lock the electrical plug unit to the lamp socket unit and the collar.

Further, the lampshade is made of light-transmissive ceramic or glass, having a bottom coupling hole located on a bottom side thereof and coupled to the coupling socket.

DETAILED DESCRIPTION OF THE PREFERRED EMBODIMENT

Figure 1:
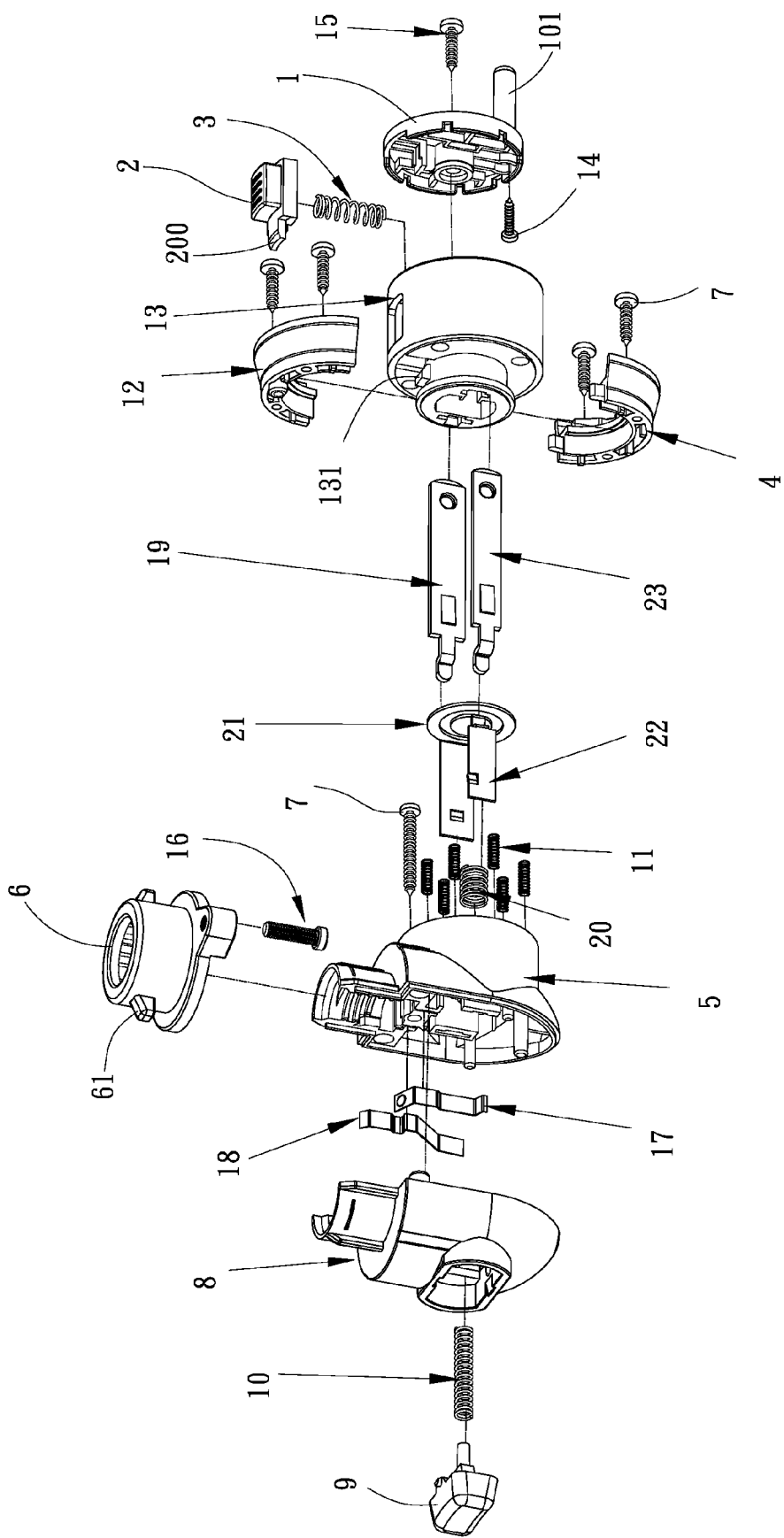
FIG. 1 is an exploded view of an angle-adjustable aroma-diffusing night lamp system in accordance with the present invention (the lampshade excluded).
Figure 2:
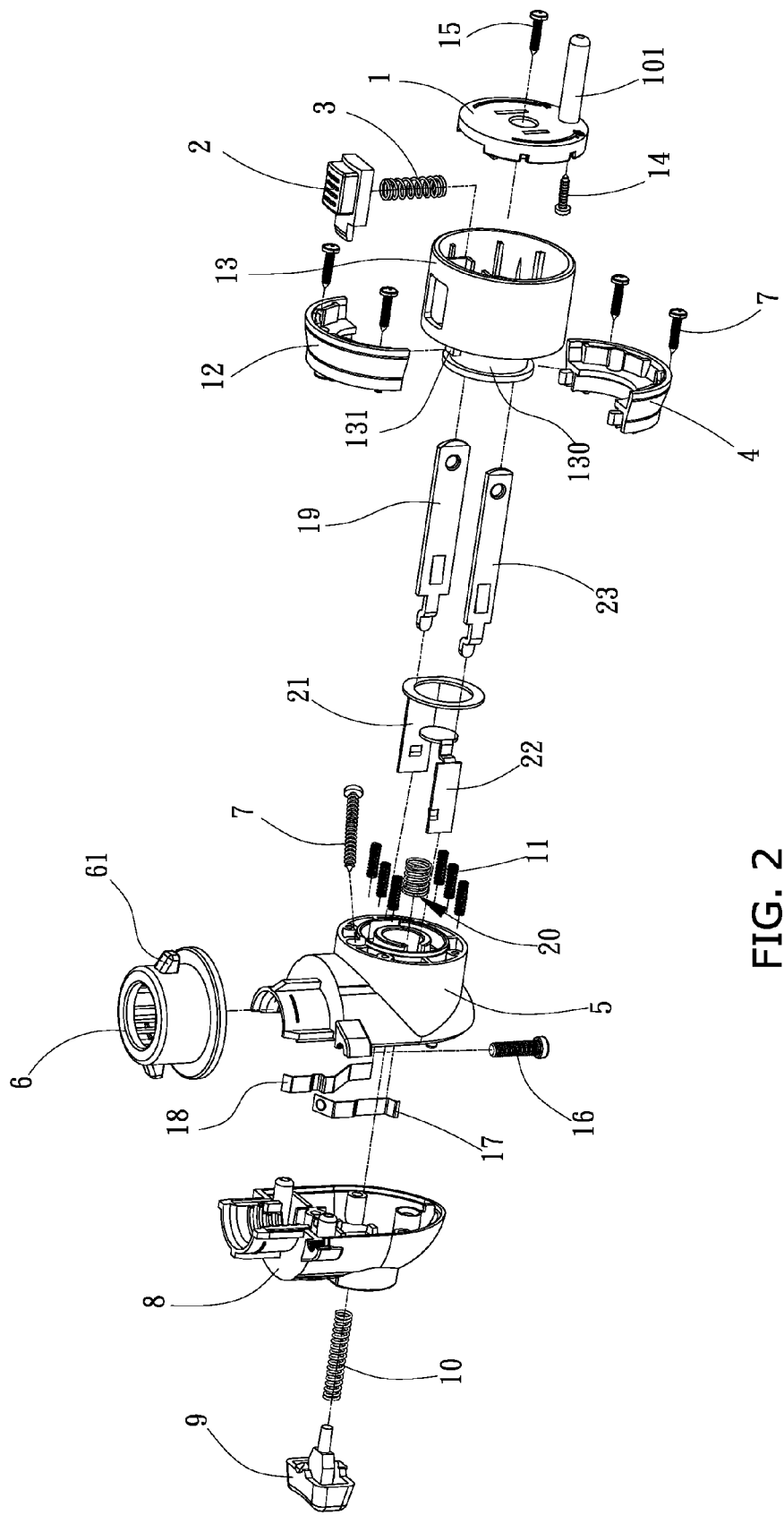
FIG. 2 corresponds to FIG. 1 when viewed from another angle (the lampshade excluded).
Figure 3C:
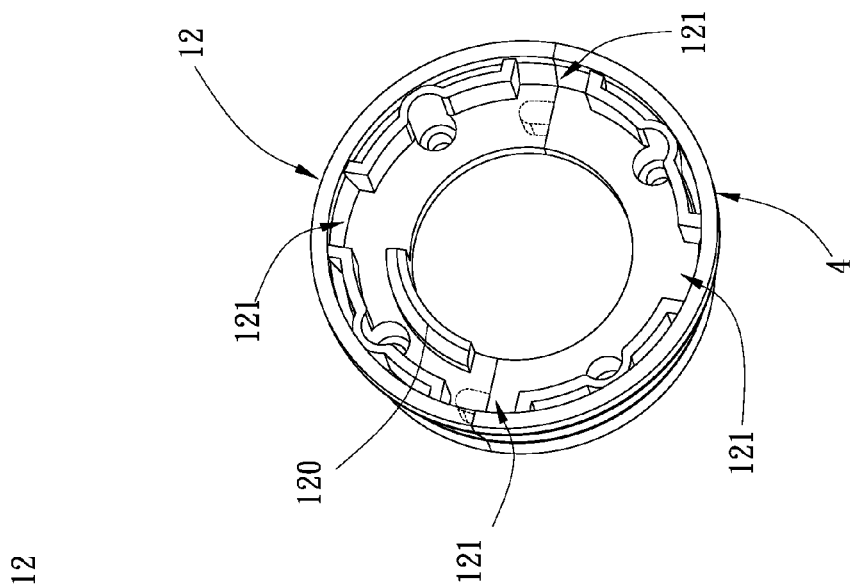
FIGS. 3A~3C illustrate the structure of the collar for angle-adjustable aroma-diffusing night lamp system in accordance with the present invention.
Figure 3B:
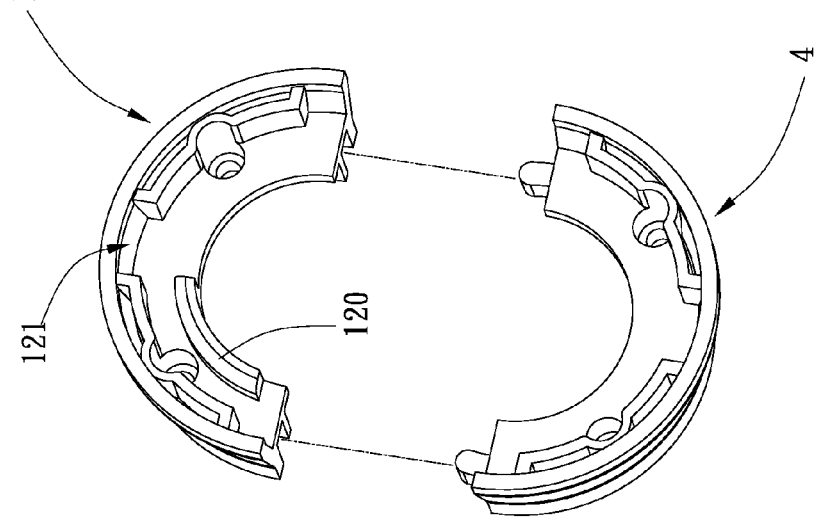
Figure 3A:
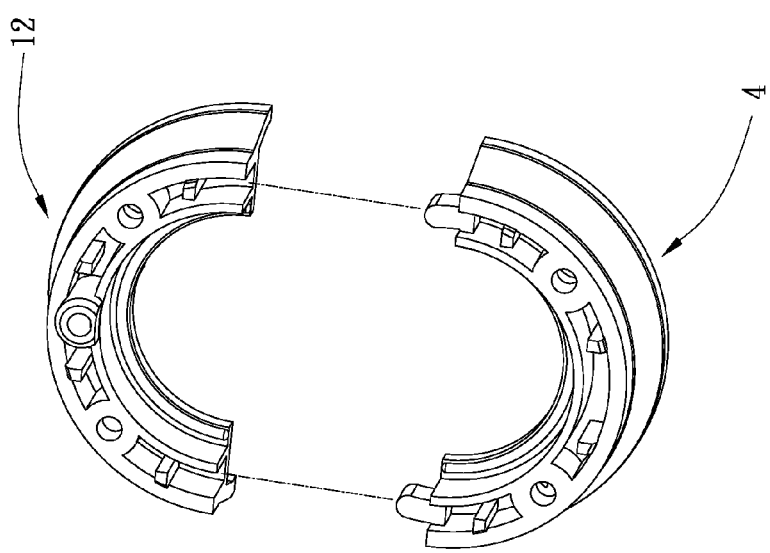
Figure 4A:
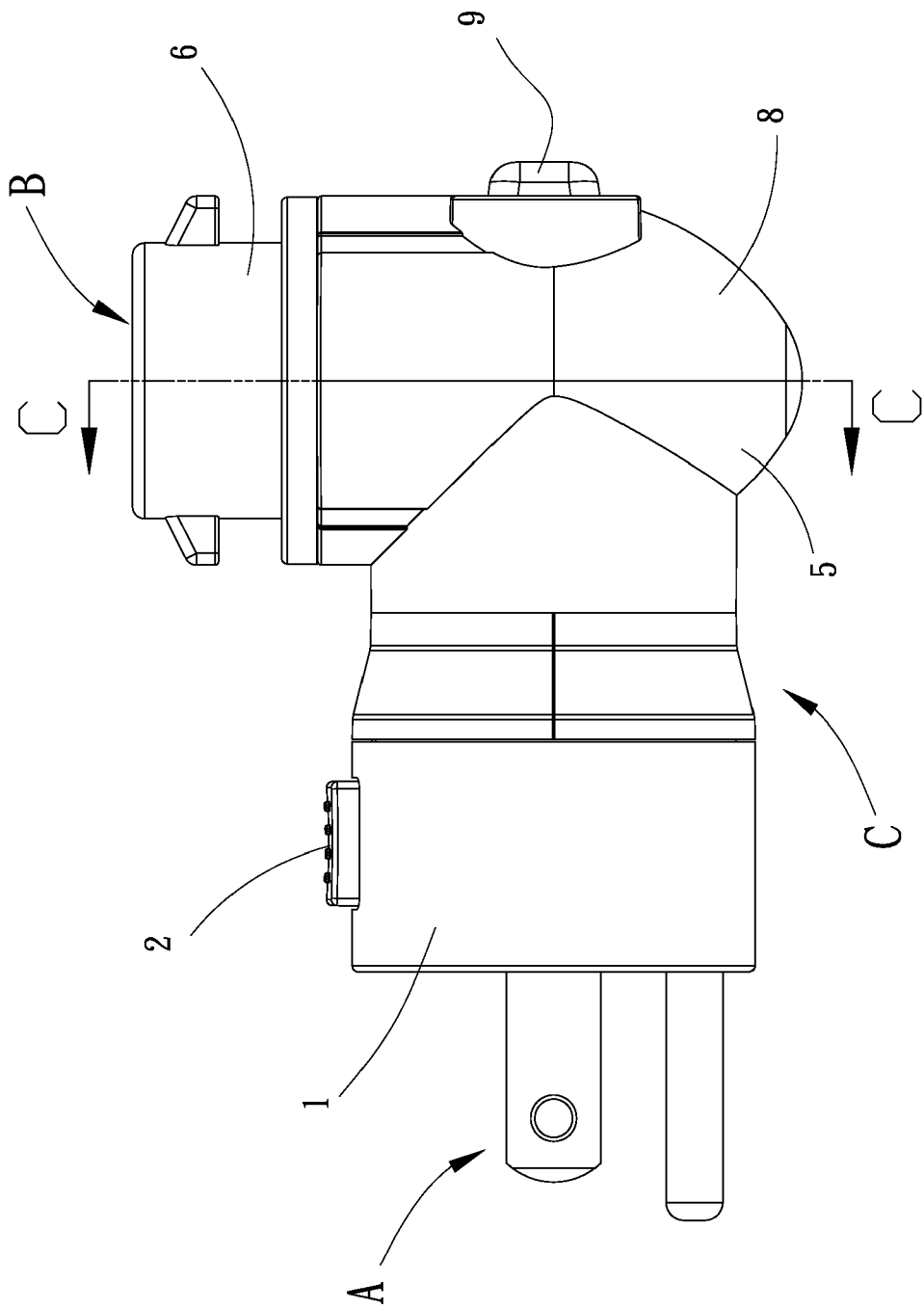
FIG. 4A is a side view of the angle-adjustable aroma-diffusing night lamp system in accordance with the present invention (the lampshade excluded).
Figure 4B:
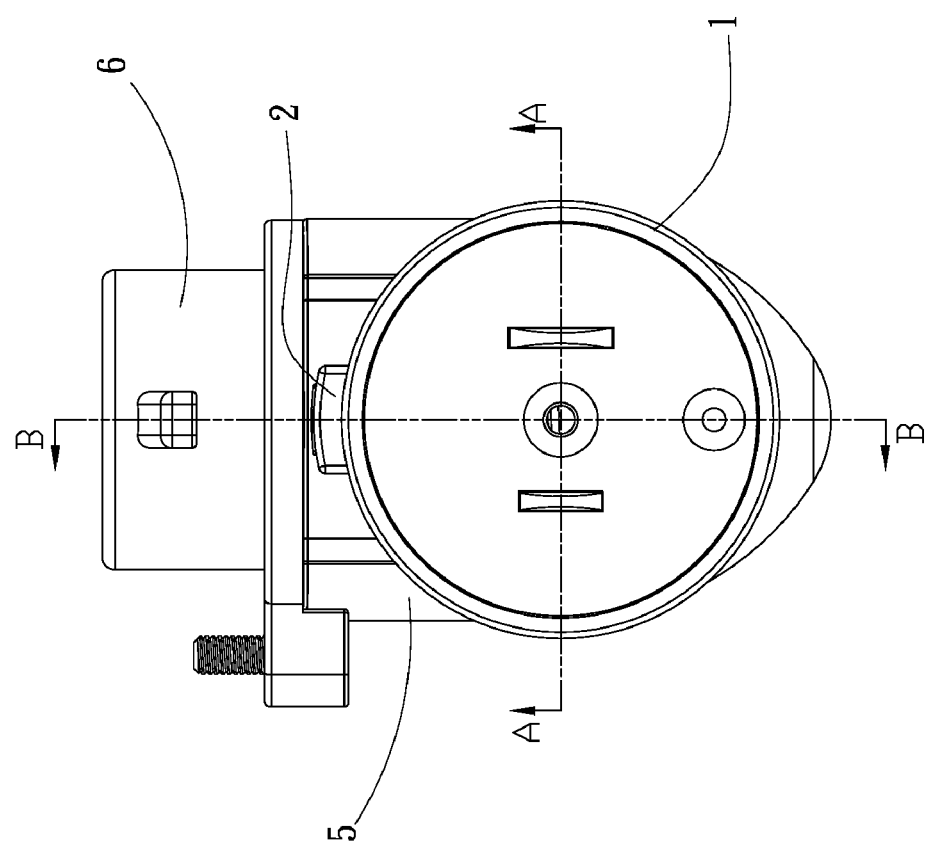
FIG. 4B is an end view of the angle-adjustable aroma-diffusing night lamp system in accordance with the present invention (the lampshade excluded).
Figure 5:
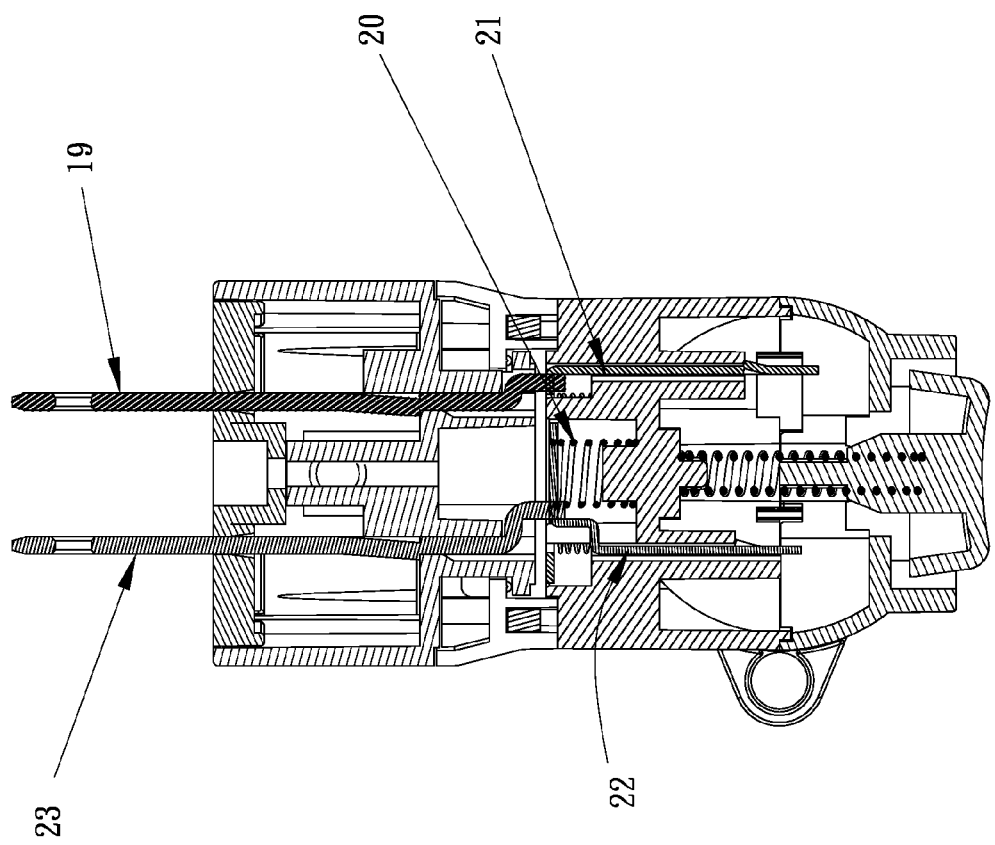
FIG. 5 is a sectional view taken along line A-A of FIG. 4B.
Figure 6:
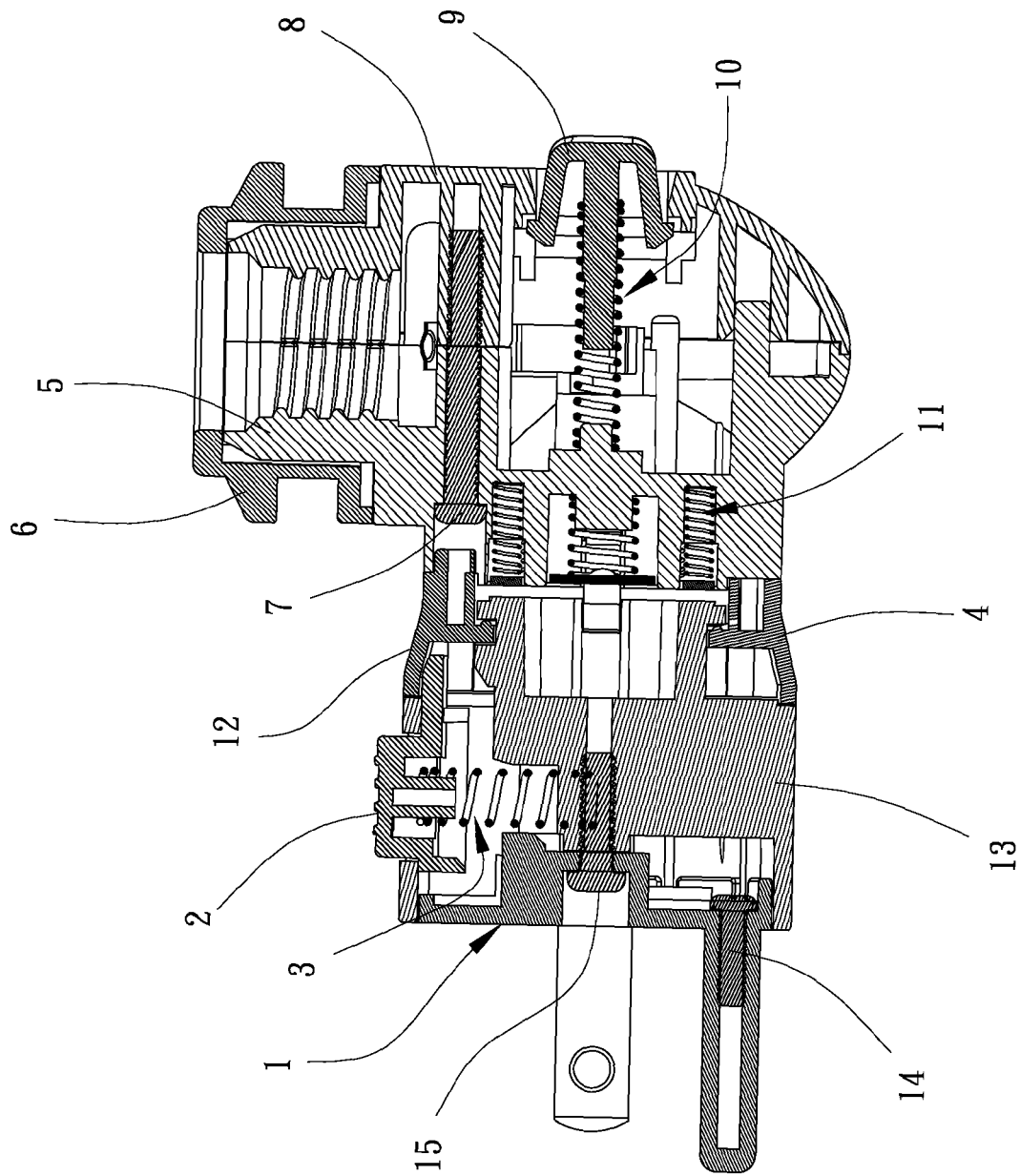
FIG. 6 is a sectional view taken along line B-B of FIG. 4B.
Figure 7:
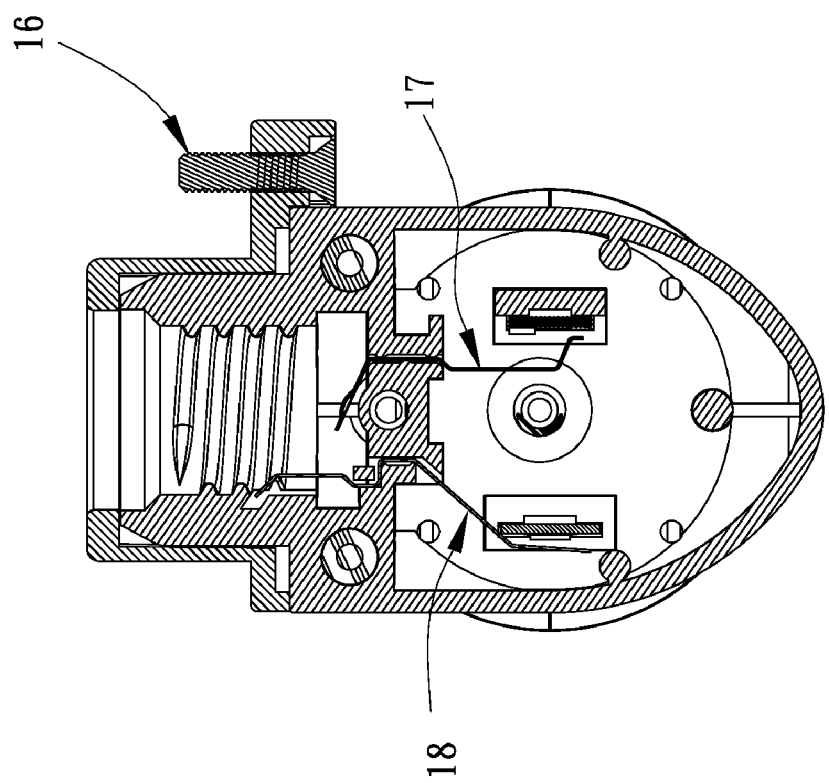
FIG. 7 is a sectional view taken along line C-C of FIG. 4A.
Figure 8:
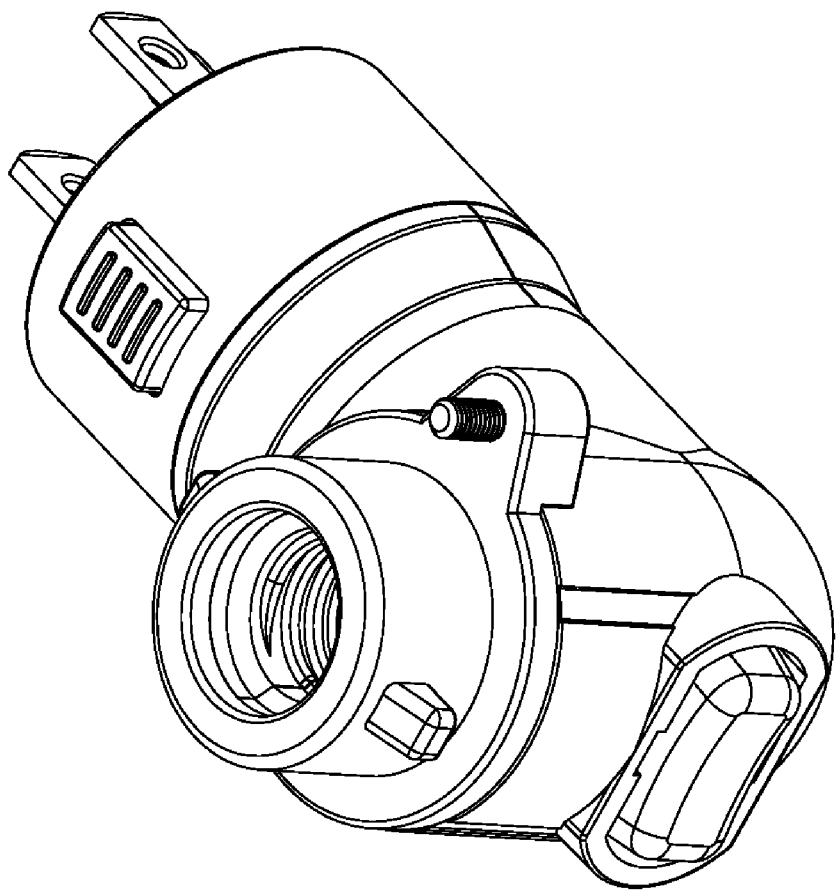
FIG. 8 illustrates the outer appearance of the angle-adjustable aroma-diffusing night lamp system in accordance with the present invention when viewed from different angles after removal of the lampshade (I).
Figure 9:
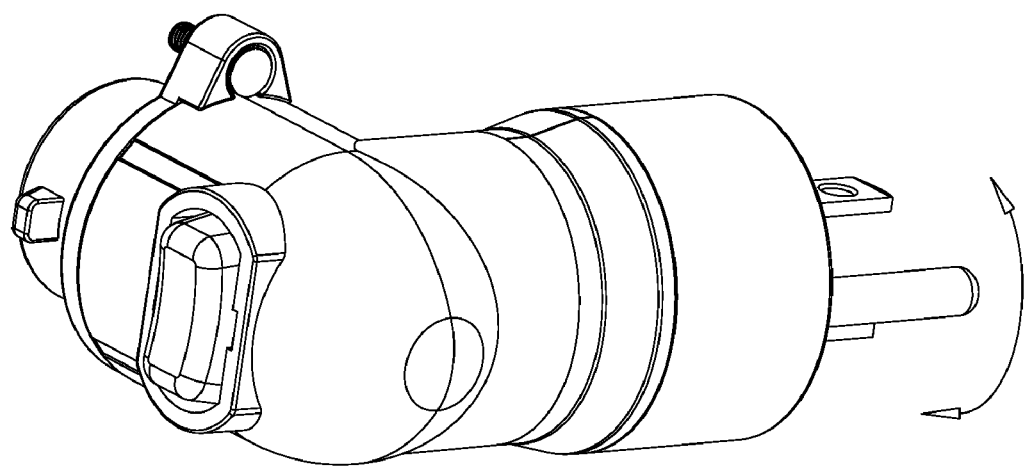
FIG. 9 illustrates the outer appearance of the angle-adjustable aroma-diffusing night lamp system in accordance with the present invention when viewed from different angles after removal of the lampshade (I).

Referring to FIG. 4, an angle-adjustable aroma-diffusing night lamp system in accordance with the present invention is shown comprising an electrical plug unit A for connection to an electrical outlet for power input, a lamp socket unit B for holding a lamp bulb (not shown) and transferring electric current from the electrical plug unit A to the lamp bulb for causing the lamp bulb to emit light, and a collar C, which is coupled to one end of the electrical plug unit A and affixed to the lamp socket unit B to secure the lamp socket unit B to the electrical plug unit A, allowing adjustment of the angle of the lamp socket unit B relative to the electrical plug unit A.

Referring to FIGS. 1~3 and 5~7 and FIG. 4 again, the electrical plug unit A comprises an electrically insulative plug housing 13, an electrically insulative cover plate 1 affixed to the bottom side of the electrically insulative plug housing 13 with a screw 15, a grounding prong 101 perpendicularly affixed to the electrically insulative cover plate 1 with a screw 14, and a positive contact blade 23 and a negative contact blade 19 mounted in the electrically insulative plug housing 13 and inserted through the electrically insulative cover plate 1 in a parallel manner relative to the grounding prong 101.

Referring to FIGS. 1~7 again, the lamp socket unit B comprises an electrically insulative socket housing consisting of an upper socket housing cover shell 8 and a lower socket housing cover shell 5 that are fixedly fastened together with a self-tapping screw 7, a positive copper strip 17 and a negative copper strip 18 mounted in the electrically insulative socket housing 8;5, a coupling socket 6 rotatably coupled to one end of the electrically insulative socket housing 8;5, a first spring member 20 mounted in the electrically insulative socket housing 8;5 at the center and at one side relative to the positive copper strip 17 and negative copper strip 18, a center contact 22 mounted in the electrically insulative socket housing 8;5 and supported on the first spring member 20 for contacting the positive copper strip 17, a plurality of second spring members 11 mounted in the electrically insulative socket housing 8;5 and equiangularly spaced around the first spring member 20, a ring contact 21 supported on the second spring members 11 and spaced around the center contact 22 and electrically connected to the negative copper strip 18, a third spring member 10 mounted in the electrically insulative socket housing 8;5 at one opposite side relative to the positive copper strip 17 and negative copper strip 18 and a push button 9 supported on the third spring member 10 and operable to control contact between the enter contact 22 and the positive copper strip 17. Subject to the effect of the first spring member 20 and the second spring members 11, the center contact 22 and the ring contact 21 are respectively kept in positive contact with the positive contact blade 23 and the negative contact blade 19.

A lamp bulb (not shown) can be inserted into the coupling socket 6 and threaded into the electrically insulative socket housing 8;5 to keep the ring contact and tip contact of the lamp bulb into contact with the positive copper strip 17 and negative copper strip 18 respectively. After installation of a lamp bulb (not shown) in the electrically insulative socket housing 8;5 of the lamp socket unit B, the user can operate the push button 9 to switch on/off the lamp bulb.

Figure 10:
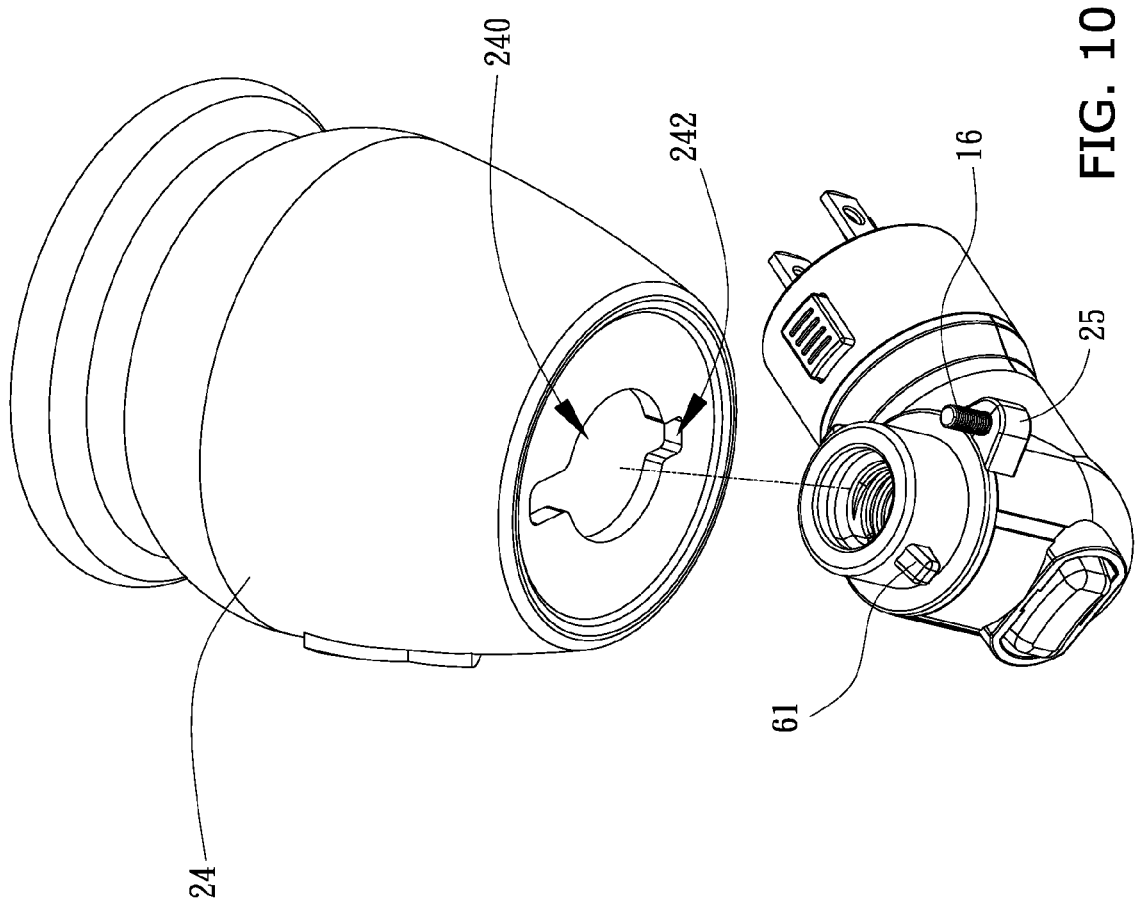
FIG. 10 is an exploded view of an angle-adjustable aroma-diffusing night lamp system in accordance with the present invention.

Referring to FIG. 10, a lampshade 24 has a shadow fluid trough (not shown) defined in the top side thereof for holding a fluid aromatic substance (such as essential oil, fragrant wax or the like), and a bottom coupling hole 240 located on the bottom side thereof. By means of the bottom coupling hole 240, the lampshade 24 is coupled to the coupling socket 6 around the lamp bulb (not shown). Further, the coupling socket 6 has two mounting blocks 61 radially protruded from the periphery thereof at two opposite sides. After insertion of the coupling socket 6 into the bottom coupling hole 240 of the lampshade 24 to move the mounting blocks 61 through a respective notch 242 on the border of the bottom coupling hole 240, the lampshade 24 is rotated through, for example, 90° angle, to let the two mounting blocks 61 be stopped at the inner surface of the bottom wall of the lampshade 24 and then a screw 16 is mounted in a screw hole 25 in the upper socket housing cover shell 8 and lower socket housing cover shell 5 and inserted into one notch 242 to stop the lampshade 24 from rotation relative to the upper socket housing cover shell 8 and lower socket housing cover shell 5, avoiding a child from touching the lamp bulb and assuring a high level of safety of the use of the product. Further, the lampshade 24 is made of light-transmissive ceramic or glass. When switched on the lamp bulb, radiating heat is transferred to the shadow fluid trough to heat the fluid aromatic substance (such as essential oil, fragrant wax or the like), causing evaporation of the fluid aromatic substance.

Referring also to FIGS. 1-6 again, the collar C is formed of a left collar half 12 and a right collar half 4. During installation, the left collar half 12 and the right collar half 4 are attached to the front coupling neck 130 and abutted against each other, and then fixedly fastened to the lower socket housing cover shell 5 of the lamp socket unit B with screws 7 to keep the positive contact blade 23 and negative contact blade 19 of the electrical plug unit A in contact with the center contact 22 and the ring contact 21 respectively and to secure the electrical plug unit A to the lamp socket unit B, allowing rotation of the electrical plug unit A relative to the lamp socket unit B. The angle of rotation of the electrical plug unit A relative to the lamp socket unit B is preferably limited to 270° angle, avoiding accidental falling of the fluid aromatic substance out of the shadow fluid trough of the lampshade 24. To achieve this function, the collar C is made having an arched stop block 120 that is located on the inside of, for example, the left collar half 12; the electrically insulative plug housing 13 comprising a peg 131 located on the periphery of the front coupling neck 130. Thus, when rotating the electrical plug unit A relative to the lamp socket unit B and the collar C, the peg 131 will be stopped at one of two distal ends of the arched stop block 120 to limit the angle of rotation.

Referring also to FIGS. 1~6 again, the collar C further comprises a plurality of equiangularly spaced latch holes 121. Further, the electrical plug unit A further comprises a spring member 3 mounted in the electrically insulative plug housing 13, and a latch 2 supported on the spring member 3 and selectively engaged into one of the latch holes 121 to lock the electrical plug unit A to the lamp socket unit B and the collar C. The latch 2 has a beveled front tip 200, facilitating engagement into one latch hole 121. The spring member 3 imparts a pressure to the latch 2, forcing the latch 2 into engagement with one latch hole 121. When wishing to adjust the angular position of the electrical plug unit A relative to the lamp socket unit B and the collar C, press the latch 2 against the spring member 3 to disengage the beveled front tip 200 from the latch hole 121, and then rotate the electrical plug unit A relative to the lamp socket unit B and the collar C to the desired angle, and then release the hand from the latch 2, enabling the latch 2 to be moved back to force the beveled front tip 200 from another latch hole 121. Further, the number of the latch holes 121 is not limited. By means of increasing the number of the latch holes 121, more angular positions can be provided for selection.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. An angle-adjustable aroma-diffusing night lamp system, comprising an electrical plug unit for connection to an electrical outlet for power input, a lamp socket unit for holding a lamp bulb and transferring electric current from the electrical plug unit to the lamp bulb for causing the lamp bulb to emit light, and a collar coupled to one end of said electrical plug unit and affixed to said lamp socket unit to secure said lamp socket unit to said electrical plug unit, wherein said electrical plug unit comprises an electrically insulative plug housing, said electrically insulative plug housing comprising a front coupling neck coupled to said collar and an electrically insulative cover plate affixed to a bottom side of said electrically insulative plug housing, and a positive contact blade and a negative contact blade mounted in said electrically insulative plug housing and inserted through said electrically insulative cover plate for connection to a city power supply outlet;

said lamp socket unit comprises an electrically insulative socket housing, a positive copper strip and a negative copper strip mounted in said electrically insulative socket housing, a coupling socket rotatably coupled to one end of said electrically insulative socket housing, a first spring member mounted in said electrically insulative socket housing at the center and at one side relative to said positive copper strip and said negative copper strip, a center contact mounted in said electrically insulative socket housing and supported on said first spring member for contacting said positive copper strip and forced by said first spring member into positive contact with said negative contact blade, a plurality of second spring members mounted in said electrically insulative socket housing and equiangularly spaced around said first spring member, a ring contact supported on said second spring members and spaced around said center contact and electrically connected to said negative copper strip and forced by said second spring members into positive contact with said negative contact blade, a third spring member mounted in said electrically insulative socket housing at one opposite side relative to said positive copper strip and negative copper strip and a push button supported on said third spring member and operable to control contact between said enter contact and said positive copper strip;

said collar is rotatably coupled to the front coupling neck of said electrically insulative housing, whereby to be rotated through an angle, between said electrical plug unit and said lamp socket unit.

2. The angle-adjustable aroma-diffusing night lamp system as claimed in claim 1, wherein said electrical plug unit further comprises a grounding prong fixedly mounted in said electrically insulative cover plate in a parallel manner relative to said positive contact blade and said negative contact blade for grounding.

3. The angle-adjustable aroma-diffusing night lamp system as claimed in claim 1, wherein said electrically insulative socket housing comprises an upper socket housing cover shell, a lower socket housing cover shell, and a self-tapping screw fastening said upper socket housing cover shell and said lower socket housing cover shell together.

4. The angle-adjustable aroma-diffusing night lamp system as claimed in claim 1, wherein said collar further comprises a plurality of equiangularly spaced latch holes; said electrical plug unit further comprises a spring member mounted in said electrically insulative plug housing, and a latch supported on the spring member of said electrical plug unit and selectively engaged into one of said latch holes to lock said electrical plug unit to said lamp socket unit and said collar.

5. The angle-adjustable aroma-diffusing night lamp system as claimed in claim 4, wherein said latch has a beveled front tip for engaging into one said latch hole 121.

6. The angle-adjustable aroma-diffusing night lamp system as claimed in claim 1, wherein said lampshade is selected from a material group of light-transmissive ceramic and glass, having a bottom coupling hole located on a bottom side thereof and coupled to said coupling socket.

7. The angle-adjustable aroma-diffusing night lamp system as claimed in claim 1, wherein said front coupling neck comprising a peg, said peg located on the periphery of said front coupling neck.

8. The angle-adjustable aroma-diffusing night lamp system as claimed in claim 7, wherein said collar comprising an arched stop block for stopping against said peg to limit the angle of rotation between said electrical plug unit and said lamp socket unit to a predetermined range.

9. The angle-adjustable aroma-diffusing night lamp system as claimed in claim 1, wherein further including a lampshade, said lampshade coupled to said lamp socket unit around the lamp bulb in said lamp socket unit and having a shadow fluid trough defined in a top side thereof for holding a fluid aromatic substance for heating by radiating heat from said lamp bulb.

10. The angle-adjustable aroma-diffusing night lamp system as claimed in claim 9, wherein said lampshade including at least a respective notch; said coupling socket including two mounting blocks radially protruded from the periphery thereof at two opposite sides; after insertion of the coupling socket into the bottom coupling hole of the lampshade to move the mounting blocks through said respective notch on the border of the bottom coupling hole, the lampshade is rotated through an angle, to let the two mounting blocks be stopped at the inner surface of the bottom wall of the lampshade and then a screw is mounted in a screw hole in the upper socket housing cover shell and lower socket housing cover shell and inserted into said notch to stop the lampshade from rotation relative to the upper socket housing cover shell and lower socket housing cover shell.

* * * * *